(12) United States Patent
Maliani

(10) Patent No.: US 10,885,170 B1
(45) Date of Patent: Jan. 5, 2021

(54) METHODS, SYSTEMS, AND STORAGE MEDIA FOR MANAGING PATIENT INFORMATION USING A BLOCKCHAIN NETWORK

(71) Applicant: Apotheka Systems Inc., Beverly Hills, CA (US)

(72) Inventor: Dennis Maliani, Marina Del Rey, CA (US)

(73) Assignee: Apotheka Systems Inc., Beverly Hills, CA (US)

( * ) Notice: Subject to any disclaimer, the term of this patent is extended or adjusted under 35 U.S.C. 154(b) by 0 days.

(21) Appl. No.: 16/196,900

(22) Filed: Nov. 20, 2018

(51) Int. Cl.
  *G06F 21/32* (2013.01)
  *H04L 9/06* (2006.01)
  *G16H 10/60* (2018.01)

(52) U.S. Cl.
  CPC ............ *G06F 21/32* (2013.01); *G16H 10/60* (2018.01); *H04L 9/0637* (2013.01); *H04L 9/0643* (2013.01); *H04L 2209/38* (2013.01)

(58) Field of Classification Search
  CPC ..... G06F 21/32; H04L 9/0637; H04L 9/0643; H04L 2209/38; G16H 10/60
  USPC ........................................................... 705/50
  See application file for complete search history.

(56) References Cited

U.S. PATENT DOCUMENTS

| | | | | |
|---|---|---|---|---|
| 5,870,723 | A * | 2/1999 | Pare, Jr. ................. | G06F 21/86 705/39 |
| 8,732,825 | B2 * | 5/2014 | Park ..................... | G06F 21/562 726/22 |
| 9,237,014 | B2 * | 1/2016 | Leung .................... | H04L 9/0643 |
| 2003/0041242 | A1 * | 2/2003 | Patel ..................... | H04L 9/3242 713/170 |
| 2014/0379373 | A1 * | 12/2014 | Vinals .................... | G16H 10/60 705/3 |
| 2016/0085916 | A1 * | 3/2016 | Smith .................... | G06F 19/00 705/3 |

(Continued)

OTHER PUBLICATIONS

"Authenticating Health Activity Data Using Distributed Ledger Technologies"; James Brogan, Immanuel Baskaran, Navin Ramachandran; Authenticating Health Activity Data Using Distributed Ledger Technologies.pdf (Year: 2018).*

(Continued)

*Primary Examiner* — Patrick McAtee
*Assistant Examiner* — Edgar R Martinez-Hernandez

(57) ABSTRACT

A system receives, from a patient, first biometric data associated with a first biometric data type and second biometric data associated with a second biometric data type and generates a cryptographic hash of the first biometric data and the second biometric data. The system records the biometric numeric score on a blockchain network. The system receives protected health information for the patient and generates a protected health information numeric score based on the protected health information for the patient. The system records the protected health information numeric score on the blockchain network, receives encrypted patient credentials, records the encrypted patient credentials on the blockchain network and generates a master cryptographic hash based at least in part on the recorded biometric numeric score. The system validates, via a validation module including a smart contract operating on the blockchain network, the patient credentials.

20 Claims, 8 Drawing Sheets

(56) References Cited

U.S. PATENT DOCUMENTS

| | | | |
|---|---|---|---|
| 2016/0239616 A1* | 8/2016 | Usami ................... | G16H 40/20 |
| 2017/0141920 A1* | 5/2017 | Herder, III ............ | G06F 21/575 |
| 2018/0046766 A1* | 2/2018 | Deonarine ............ | H04L 9/0643 |
| 2018/0060496 A1* | 3/2018 | Bulleit ................. | H04L 9/3239 |
| 2018/0082023 A1* | 3/2018 | Curbera ............. | G06F 19/3418 |
| 2018/0082024 A1 | 3/2018 | Curbera | |
| 2018/0211058 A1 | 7/2018 | Aunger | |
| 2018/0211718 A1* | 7/2018 | Heath .................. | A01K 29/005 |
| 2019/0035492 A1* | 1/2019 | Finkelstein ........ | G06K 9/00288 |

OTHER PUBLICATIONS

"Rolled versus Plain Fingerprints: Matching with Cryptographic One-way Hashes"; Qinghai Gao, Cheng Zhang; Rolled versus Plain Fingerprints: Matching with Cryptographic One-way Hashes.PDF (Year: 2017).*

"Secure Method for Biometric-Based Recognition with Integrated Cryptographic Functions"; Shin-Yan Chiou Secure Method for Biometric-Based Recognition with Integrated Cryptographic Functions. PDF(Year: 2013).*

* cited by examiner

METHODS, SYSTEMS, AND STORAGE MEDIA FOR MANAGING PATIENT INFORMATION USING A BLOCKCHAIN NETWORK

TECHNICAL FIELD

The present disclosure relates to blockchain technologies and more specifically to a blockchain-based iterative validation process.

BACKGROUND

In the United States, most people believe that Health Insurance Portability and Accountability Act (HIPAA) laws keep medical records private, shared only amongst doctors, ourselves, and maybe a loved one or caregiver. But those who believe that may be surprised to learn that others have access to their records and do not need anyone's consent to do so. In fact, there are dozens of individuals and organizations that are legally allowed to access private medical records for a variety of reasons, either by request or by purchase. In some cases, patients provide permission for their access. In others, permission isn't necessary. In still other cases, patients provide permission without even realizing it.

Some entities access our records illegally. According to the U.S. Department of Health and Human Services, there were no less than 2,181 healthcare data breaches between 2009 and 2017 resulting in the exposure of 176,709,305 medical records.

There are two general types of medical records that are shared or purchased. The first type is called an individually identifiable record, which focuses on personal attributes, such as a record with a person's name, doctors, insurers, diagnoses, treatments, and more. This is the record we request when we want to review our own medical records. The second type comes in a format called an aggregated medical record. An aggregated medical record is a database of attributes, but is not used to identify any one individual per se. Instead, hundreds or thousands of records are compiled into several lists to make up one aggregated list. That process is called "data mining." For example, a hospital may decide to mine data of all of the records of patients who have had a heart bypass surgery. The aggregated record may be comprised of hundreds of patients, categorized by types of insurance and further sub-categorized by primary care doctors, surgeons, and numerous other possible categories. As opposed to individually identifiable records, an aggregated medical record is "de-identified," meaning that neither your identity nor any medical procedure, diagnosis, or practitioner in your records is disclosed.

Under HIPAA, certain individuals and entities have the right to access patient medical records. They are classified as covered entities under HIPAA, meaning that they have the right to access the records under specific regulatory guidelines. Covered entities include doctors and allied medical professionals, facilities (like hospitals, labs, and nursing homes), payers (like Medicare and health insurance), technology providers that maintain electronic health records, and the government.

As covered entities, they have very strict rules they must follow, and that includes getting written permission from patients to share their records. Under HIPAA, the general guidelines are as follows: (1) You have a legal right to copies of your own medical records; (2) A loved one or caregiver may have the right to get copies of your medical records, but you may have to provide written permission; (3) Your health care providers have a right to see and share your records with anyone else to whom you've granted permission. For example, if your primary care doctor refers you to a specialist, you may be asked to sign a form that says he or she can share your records with that specialist; (4) Your payers have a right to get copies and use your medical records as specified in HIPAA laws. Insurance companies, Medicare, Medicaid, workers compensation, Social Security disability, Department of Veterans Affairs, or any institutional entity that pays for any portion of your healthcare needs may review your records; (5) Federal and state government may have a right to your medical records. In addition to medical payment, other agencies may have access, such as law enforcement and child protective services if a subpoena is obtained. If you've been in a workplace accident, the federal Occupational Safety and Health Administration (OSHA) may get involved; (6) Medical Information Bureau, also known as the MIB Group, may have an individual record on you and is not subject to HIPAA laws. The MIB Group is a non-profit entity found more than 100 years ago that provides information to life insurance to assess eligibility for coverage; and (7) Prescription databases like IntelliScript (Milliman) and MedPoint (Ingenix) will very likely have data minded records on all prescription drugs you have purchased over the past five or more years. This information is usually used by life insurance or disability insurance companies to determine whether or not they will sell you insurance.

One entity not covered under HIPAA are employers. Even if they pay for your insurance or medical care out of pocket, HIPAA prohibits them from accessing medical records or insurance claims as it could result in discrimination. In some cases, the unauthorized access to medical records is intentional and criminal. In other cases, a disclosure may be the result of the carelessness of our health provider or ourselves. Example include (1) Hackers: Hackers have gained access to thousands of private records, whether they are health records, credit card records or other sources of information. Medical information is a prime target because thieves make a lot of money from medical identity theft. Hackers are not looking for a specific individual's records; instead, they seek as many records as possible, although not aggregated; (2) Targeted illegal access: Another illegal form of access might be aimed at a specific individual's records. A business might pay someone under the table to get hold of a potential employee's medical record, or a soon-to-be-divorced spouse might seek information on the one he or she is divorcing. (3) Accidental leaks: There are other ways our private medical information might unintentionally become public, even though that makes it no less egregious. A leased copy machine in a doctor's office is returned to the leasing company with thousands of copied paper medical records in its memory. The same thing can happen with computer hard drives that have failed. But just because the drives don't work with that computer anymore doesn't mean someone can't retrieve the data.

When records are put together in an aggregated form, they can be used for a variety of reasons. Regardless, these organizations have a right to aggregate the information and share or sell it, as long as it has been de-identified. Some uses include: (1) Research: Aggregated data may be used in research. The conclusions reached by using the data can help patients of the future; (2) Selling data: Sometimes hospitals and other covered entities will sell their aggregated data. A hospital sells its data about a thousand patients who had back surgery to a company that sells wheelchairs. A pharmacy sells its data about its 5,000 customers who filled cholesterol drug prescriptions to the local heart center. Aggregated data are used for marketing purposes in ways too numerous to list and are a large source of revenue for many of the organizations that work with patients; and (3) Outreach and fundraising: Nonprofit and charitable organizations may use aggregated data to help with fundraising. Local organizations may team up with the hospitals or other facilities that aggregate their data. State, national or international organizations find other ways to access this aggregated data as well. Of course, we find ourselves on their fundraising lists when we take an interest in their cause, which means they can also aggregate their own data to sell to other organizations that want to know that we took an interest in.

As can be appreciated, there are many different ways that private medical data can be accessed, hacked, and used. What is needed is an improved mechanism of managing the security and accessibility of medical records.

BRIEF DESCRIPTION OF THE DRAWINGS

Various embodiments in accordance with the present disclosure will be described with reference to the drawings, in which.

DETAILED DESCRIPTION

Figure 1:
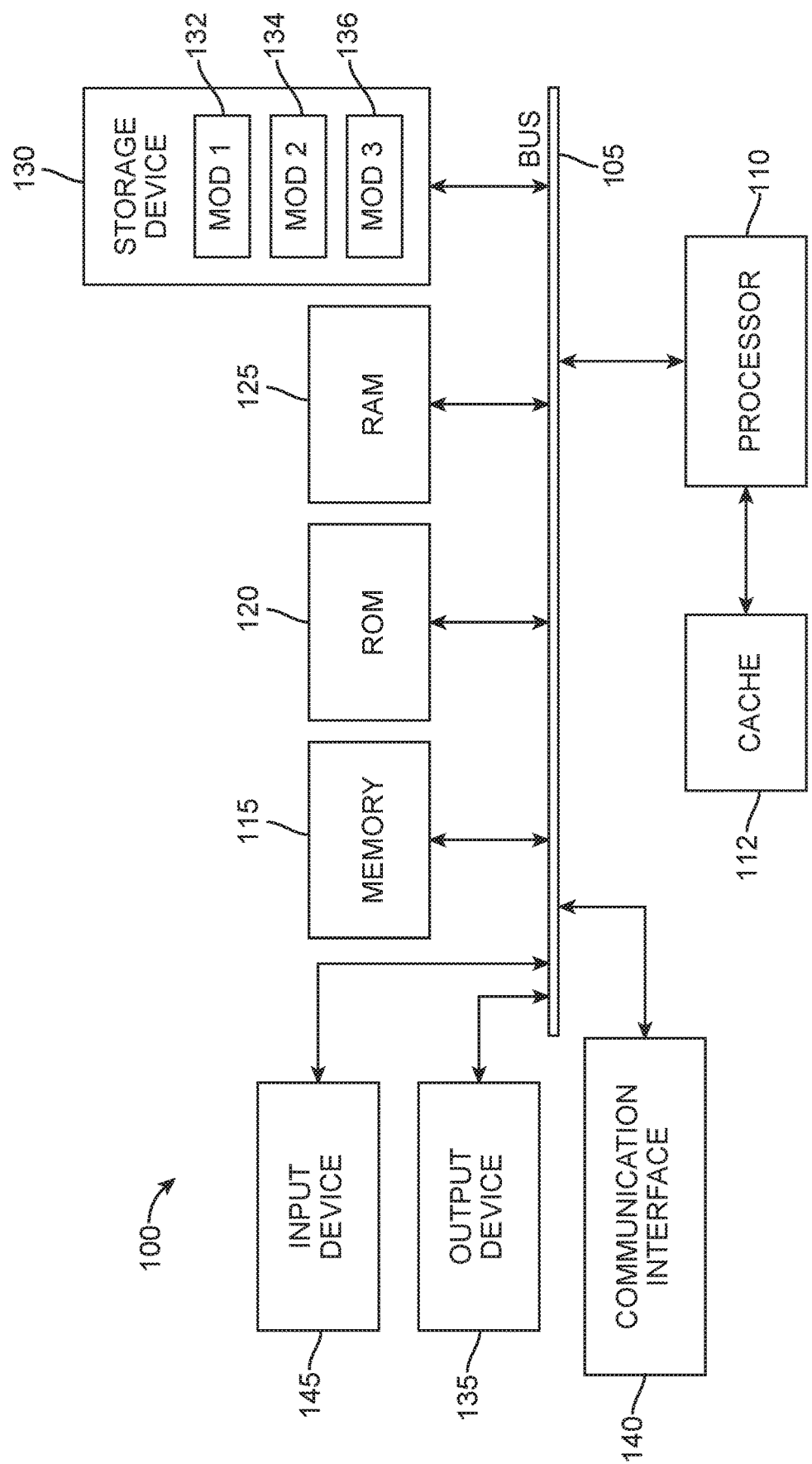
FIG. 1 illustrates an example system in which aspects of the various embodiments can be utilized.

Systems and methods in accordance with various embodiments of the present disclosure overcome one or more of the above-referenced and other deficiencies in conventional approaches related to accessing private patient data. In particular, various embodiments of the present disclosure can provide an improvement in the process of accessing patient data securely.

Various other functions and advantages are described and suggested below as may be provided in accordance with the various embodiments.

BRIEF INTRODUCTION

One aspect of the present disclosure relates to a method. The method may include receiving, from a patient, first biometric data associated with a first biometric data type and second biometric data associated with a second biometric data type. The method may include generating a cryptographic hash of the first biometric data and the second biometric data to yield a biometric numeric score. The method may include recording the biometric numeric score on a blockchain network to yield a recorded biometric numeric score. The method may include receiving protected health information for the patient. The method may include generating a protected health information numeric score based on the protected health information for the patient. The method may include recording the protected health information numeric score on the blockchain network to yield a recorded protected health information numeric score. The method may include receiving and encrypting patient credentials to yield encrypted patient credentials. The method may include recording the encrypted patient credentials on the blockchain network to yield recorded encrypted patient credentials. The method may include generating a master cryptographic hash based at least in part on the recorded biometric numeric score. The score can be a recorded protected health information, a numeric score, and/or recorded encrypted patient credentials. The method may include validating, via a validation module including a smart contract operating on the blockchain network. The patient may use the master cryptographic hash which may be based on a series of validation iterations including a first series of validation iterations limited to the protected health information, and a second series of validation iterations including the protected health information and one or more biometric data types.

Another aspect of the present disclosure relates to a system. The system may include one or more hardware processors configured by machine-readable instructions. The processor(s) may be configured to receive, from a patient, first biometric data associated with a first biometric data type and second biometric data associated with a second biometric data type. The processor(s) may be configured to generate a cryptographic hash of the first biometric data and the second biometric data to yield a biometric numeric score. The processor(s) may be configured to record the biometric numeric score on a blockchain network to yield a recorded biometric numeric score. The processor(s) may be configured to receive protected health information for the patient. The processor(s) may be configured to generate a protected health information numeric score based on the protected health information for the patient. The processor(s) may be configured to record the protected health information numeric score on the blockchain network to yield a recorded protected health information numeric score. The processor(s) may be configured to receive and encrypting patient credentials to yield encrypted patient credentials. The processor(s) may be configured to record the encrypted patient credentials on the blockchain network to yield recorded encrypted patient credentials. The processor(s) may be configured to generate a master cryptographic hash based at least in part on the recorded biometric numeric score. The processor(s) may be configured to validate, via a validation module including a smart contract operating on the blockchain network. The patient may use the master cryptographic hash which may be based on a series of validation iterations including a first series of validation iterations limited to the protected health information, and a second series of validation iterations including the protected health information and one or more biometric data types.

Yet another aspect of the present disclosure relates to a non-transient computer-readable storage medium having instructions embodied thereon, the instructions being executable by one or more processors to perform a method. The method may include receiving, from a patient, first biometric data associated with a first biometric data type and second biometric data associated with a second biometric data type. The method may include generating a cryptographic hash of the first biometric data and the second biometric data to yield a biometric numeric score. The method may include recording the biometric numeric score on a blockchain network to yield a recorded biometric numeric score. The method may include receiving protected health information for the patient. The method may include generating a protected health information numeric score based on the protected health information for the patient. The method may include recording the protected health information numeric score on the blockchain network to yield a recorded protected health information numeric score. The method may include receiving and encrypting patient credentials to yield encrypted patient credentials. The method may include recording the encrypted patient credentials on the blockchain network to yield recorded encrypted patient credentials. The method may include generating a master cryptographic hash based at least in part on the recorded biometric numeric score. The method may include validating, via a validation module including a smart contract operating on the blockchain network. The patient may use the master cryptographic hash which may be based on a series of validation iterations including a first series of validation iterations limited to the protected health information, and a second series of validation iterations including the protected health information and one or more biometric data types.

Another aspect of the present disclosure relates to another method. The method may include receiving personal health information associated with a patient to be validated in a medical record system. The method may include validating the personal health information of the patient by determining whether a match exists with a cryptographic hash of previously entered personal health information of patients. The cryptographic hash may be recorded on a blockchain network. The method may include, when a match exception exists based on the personal health information of the patient, implementing a process of validation iterations which includes determining a match of received biometric data from the patient against a cryptographic hash of a biometric numeric score recorded on the blockchain network. The biometric numeric score may represent a sub data point representing a type of biometric data used to validate the patient.

Another aspect of the present disclosure relates to a system. The system may include one or more hardware processors configured by machine-readable instructions. The processor(s) may be configured to receive personal health information associated with a patient to be validated in a medical record system. The processor(s) may be configured to validate the personal health information of the patient by determining whether a match exists with a cryptographic hash of previously entered personal health information of patients. The cryptographic hash may be recorded on a blockchain network. The processor(s) may be configured to, when a match exception exists based on the personal health information of the patient, implement a process of validation iterations which includes determining a match of received biometric data from the patient against a cryptographic hash of a biometric numeric score recorded on the blockchain network. The biometric numeric score may represent a sub data point representing a type of biometric data used to validate the patient.

Yet another aspect of the present disclosure relates to a non-transient computer-readable storage medium having instructions embodied thereon, the instructions being executable by one or more processors to perform a method. The method may include receiving personal health information associated with a patient to be validated in a medical record system. The method may include validating the personal health information of the patient by determining whether a match exists with a cryptographic hash of previously entered personal health information of patients. The cryptographic hash may be recorded on a blockchain network. The method may include, when a match exception exists based on the personal health information of the patient, implementing a process of validation iterations which includes determining a match of received biometric data from the patient against a cryptographic hash of a biometric numeric score recorded on the blockchain network. The biometric numeric score may represent a sub data point representing a type of biometric data used to validate the patient.

DETAILED DESCRIPTION

As the system disclosed herein requires computing components, a general example computing system shall be disclosed in FIG. 1, which can provide some basic hardware components making up a server, node or other computer system. FIG. 1 illustrates a computing system architecture 100 wherein the components of the system are in electrical communication with each other using a connector 105. Exemplary system 100 includes a processing unit (CPU or processor) 110 and a system connector 105 that couples various system components including the system memory 115, such as read only memory (ROM) 120 and random access memory (RAM) 125, to the processor 110. The system 100 can include a cache of high-speed memory connected directly with, in close proximity to, or integrated as part of the processor 110. The system 100 can copy data from the memory 115 and/or the storage device 130 to the cache 112 for quick access by the processor 110. In this way, the cache can provide a performance boost that avoids processor 110 delays while waiting for data. These and other modules/services can control or be configured to control the processor 110 to perform various actions. Other system memory 115 may be available for use as well. The memory 115 can include multiple different types of memory with different The processor 110 can include any general purpose processor and a hardware module or software module/service, such as mod 1 132, mod 2 134, and mod 3 136 stored in storage device 130, configured to control the processor 110 as well as a special-purpose processor where software instructions are incorporated into the actual processor design. The processor 110 may be a self-contained computing system, for example, containing multiple cores or processors, a bus (connector), memory controller, cache, etc. A multi-core processor may be symmetric or asymmetric.

To enable user interaction with the computing device 100, an input device 145 can represent a variety of input mechanisms, such as a microphone for speech, a touch-sensitive screen for gesture or graphical input, a keyboard and/or mouse, e.g., for motion input and so forth. An output device 135 can also be one or more of a number of output mechanisms known to those of skill in the art. In some instances, multimodal systems can enable a user to provide multiple types of input to communicate with the computing device 100. The communications interface 140 can generally govern and manage the user input and system output. There is no restriction on operating on any particular hardware arrangement and therefore the basic features here may easily be substituted for improved hardware or firmware arrangements as they are developed.

Storage device 130 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 125, read only memory (ROM) 120, and/or hybrids thereof.

The storage device 130 can include software services 132, 134, 136 for controlling the processor 110. Other hardware or software modules/services are contemplated. The storage device 130 can be connected to the system connector 105. In one aspect, a hardware module that performs a particular function can include the software component stored in a computer-readable medium in connection with the necessary hardware components, such as the processor 110, connector 105, display 135, and so forth, to carry out the function.

FIG. 1 illustrates an example electronic user device 100 that can be used in accordance with various embodiments. Although a general computing device (e.g., an electronic book reader, portable device or tablet computer) is shown, it should be understood that any electronic device capable of receiving, determining, and/or processing input can be used in accordance with various embodiments discussed herein, where the devices can include, for example, desktop computers, notebook computers, personal data assistants, smart phones, video gaming consoles, television set top boxes, and portable media players. In some embodiments, a computing device can be an analog device, such as a device that can perform signal processing using operational amplifiers. In this example, the computing device 100 has a display screen 135 on the front side, which under normal operation will display information to a user facing the display screen (e.g., on the same side of the computing device as the display screen). The computing device in this example includes at least one camera 145 or other imaging element for capturing still or video image information over at least a field of view of the at least one camera. In some embodiments, the computing device might only contain one imaging element, and in other embodiments the computing device might contain several imaging elements. Each image capture element may be, for example, a camera, a charge-coupled device (CCD), a motion detection sensor, or an infrared sensor, among many other possibilities. If there are multiple image capture elements on the computing device, the image capture elements may be of different types. In some embodiments, at least one imaging element can include at least one wide-angle optical element, such as a fish eye lens, that enables the camera to capture images over a wide range of angles, such as 180 degrees or more. Further, each image capture element can comprise a digital still camera, configured to capture subsequent frames in rapid succession, or a video camera able to capture streaming video.

The example computing device 100 also includes at least one microphone 145 or other audio capture device capable of capturing audio data, such as words or commands spoken by a user of the device. In this example, a microphone 145 is placed on the same side of the device as the display screen 135, such that the microphone will typically be better able to capture words spoken by a user of the device. In at least some embodiments, a microphone can be a directional microphone that captures sound information from substantially directly in front of the microphone, and picks up only a limited amount of sound from other directions. It should be understood that a microphone might be located on any appropriate surface of any region, face, or edge of the device in different embodiments, and that multiple microphones can be used for audio recording and filtering purposes, etc.

The example computing device 100 also includes at least one orientation sensor 145, such as a position and/or movement-determining element. Such a sensor can include, for example, an accelerometer or gyroscope operable to detect an orientation and/or change in orientation of the computing device, as well as small movements of the device. An orientation sensor also can include an electronic or digital compass, which can indicate a direction (e.g., north or south) in which the device is determined to be pointing (e.g., with respect to a primary axis or other such aspect). An orientation sensor also can include or comprise a global positioning system (GPS) or similar positioning element operable to determine relative coordinates for a position of the computing device, as well as information about relatively large movements of the device. Various embodiments can include one or more such elements in any appropriate combination. As should be understood, the algorithms or mechanisms used for determining relative position, orientation, and/or movement can depend at least in part upon the selection of elements available to the device.

FIG. 1 also illustrates a logical arrangement of a set of general components of an example computing device 100 such as the device 100. In this example, the device includes a processor 110 for executing instructions that can be stored in a memory device or element YY04. As would be apparent to one of ordinary skill in the art, the device can include many types of memory, data storage, or non-transitory computer-readable storage media, such as a first data storage for program instructions for execution by the processor 110, a separate storage for images or data, a removable memory for sharing information with other devices, etc. The device typically will include some type of display element 135, such as a touch screen or liquid crystal display (LCD), although devices such as portable media players might convey information via other means, such as through audio speakers. As discussed, the device in many embodiments will include at least one image capture element 145 such as a camera or infrared sensor that is able to image projected images or other objects in the vicinity of the device. Methods for capturing images or video using a camera element with a computing device are well known in the art and will not be discussed herein in detail. It should be understood that image capture can be performed using a single image, multiple images, periodic imaging, continuous image capturing, image streaming, etc. Further, a device can include the ability to start and/or stop image capture, such as when receiving a command from a user, application, or other device. The example device similarly includes at least one audio capture component 145, such as a mono or stereo microphone or microphone array, operable to capture audio information from at least one primary direction. A microphone can be a uni- or omni-directional microphone as known for such devices.

In some embodiments, the computing device 100 of FIG. 1 can include one or more communication elements 140, such as a Wi-Fi, Bluetooth, RF, wired, or wireless communication system. The device in many embodiments can communicate with a network, such as the Internet, and may be able to communicate with other such devices. In some embodiments the device can include at least one additional input device able to receive conventional input from a user. This conventional input can include, for example, a push button, touch pad, touch screen, wheel, joystick, keyboard, mouse, keypad, or any other such device or element whereby a user can input a command to the device. In some embodiments, however, such a device might not include any buttons at all, and might be controlled only through a combination of visual and audio commands, such that a user can control the device without having to be in contact with the device.

The device 100 also can include at least one orientation or motion sensor 145. As discussed, such a sensor can include an accelerometer or gyroscope operable to detect an orientation and/or change in orientation, or an electronic or digital compass, which can indicate a direction in which the device is determined to be facing. The mechanism(s) also (or alternatively) can include or comprise a global positioning system (GPS) or similar positioning element operable to determine relative coordinates for a position of the computing device, as well as information about relatively large movements of the device. The device can include other elements as well, such as may enable location determinations through triangulation or another such approach. These mechanisms can communicate with the processor 110, whereby the device can perform any of a number of actions described or suggested herein.

As an example, a computing device such as that described with respect to FIG. 1 can capture and/or track various information for a user over time. This information can include any appropriate information, such as location, actions (e.g., sending a message or creating a document), user behavior (e.g., how often a user performs a task, the amount of time a user spends on a task, the ways in which a user navigates through an interface, etc.), user preferences (e.g., how a user likes to receive information), open applications, submitted requests, received calls, and the like. As discussed above, the information can be stored in such a way that the information is linked or otherwise associated whereby a user can access the information using any appropriate dimension or group of dimensions.

As discussed, different approaches can be implemented in various environments in accordance with the described embodiments. For example, a Web-based environment can be used for purposes of explanation, different environments may be used, as appropriate, to implement various embodiments. The system includes an electronic client device 100, which can include any appropriate device operable to send and receive requests, messages or information over an appropriate network and convey information back to a user of the device. Examples of such client devices include personal computers, cell phones, handheld messaging devices, laptop computers, set-top boxes, personal data assistants, electronic book readers and the like. The network can include any appropriate network, including an intranet, the Internet, a cellular network, a local area network or any other such network or combination thereof. Components used for such a system can depend at least in part upon the type of network and/or environment selected. Protocols and components for communicating via such a network are well known and will not be discussed herein in detail. Communication over the network can be enabled via wired or wireless connections and combinations thereof. In this example, the network includes the Internet, as the environment includes a Web server for receiving requests and serving content in response thereto, although for other networks an alternative device serving a similar purpose could be used, as would be apparent to one of ordinary skill in the art.

The illustrative environment includes at least one application server and a data store. It should be understood that there can be several application servers, layers or other elements, processes or components, which may be chained or otherwise configured, which can interact to perform tasks such as obtaining data from an appropriate data store. As used herein the term "data store" refers to any device or combination of devices capable of storing, accessing and retrieving data, which may include any combination and number of data servers, databases, data storage devices and data storage media, in any standard, distributed or clustered environment. The application server can include any appropriate hardware and software for integrating with the data store as needed to execute aspects of one or more applications for the client device and handling a majority of the data access and business logic for an application. The application server provides access control services in cooperation with the data store and is able to generate content such as text, graphics, audio and/or video to be transferred to the user, which may be served to the user by the Web server in the form of HTML, XML or another appropriate structured language in this example. The handling of all requests and responses, as well as the delivery of content between the client device and the application server, can be handled by the Web server. It should be understood that the Web and application servers are not required and are merely example components, as structured code discussed herein can be executed on any appropriate device or host machine as discussed elsewhere herein.

The data store can include several separate data tables, databases or other data storage mechanisms and media for storing data relating to a particular aspect. For example, the data store illustrated includes mechanisms for storing production data and user information, which can be used to serve content for the production side. The data store also is shown to include a mechanism for storing log or session data. It should be understood that there can be many other aspects that may need to be stored in the data store, such as page image information and access rights information, which can be stored in any of the above listed mechanisms as appropriate or in additional mechanisms in the data store. The data store is operable, through logic associated therewith, to receive instructions from the application server and obtain, update or otherwise process data in response thereto. In one example, a user might submit a search request for a certain type of element. In this case, the data store might access the user information to verify the identity of the user and can access the catalog detail information to obtain information about elements of that type. The information can then be returned to the user, such as in a results listing on a Web page that the user is able to view via a browser on the user device. Information for a particular element of interest can be viewed in a dedicated page or window of the browser.

Each server typically will include an operating system that provides executable program instructions for the general administration and operation of that server and typically will include computer-readable medium storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 1. Thus, the depiction of the system 100 in FIG. 1 should be taken as being illustrative in nature and not limiting to the scope of the disclosure.

Figure 2:
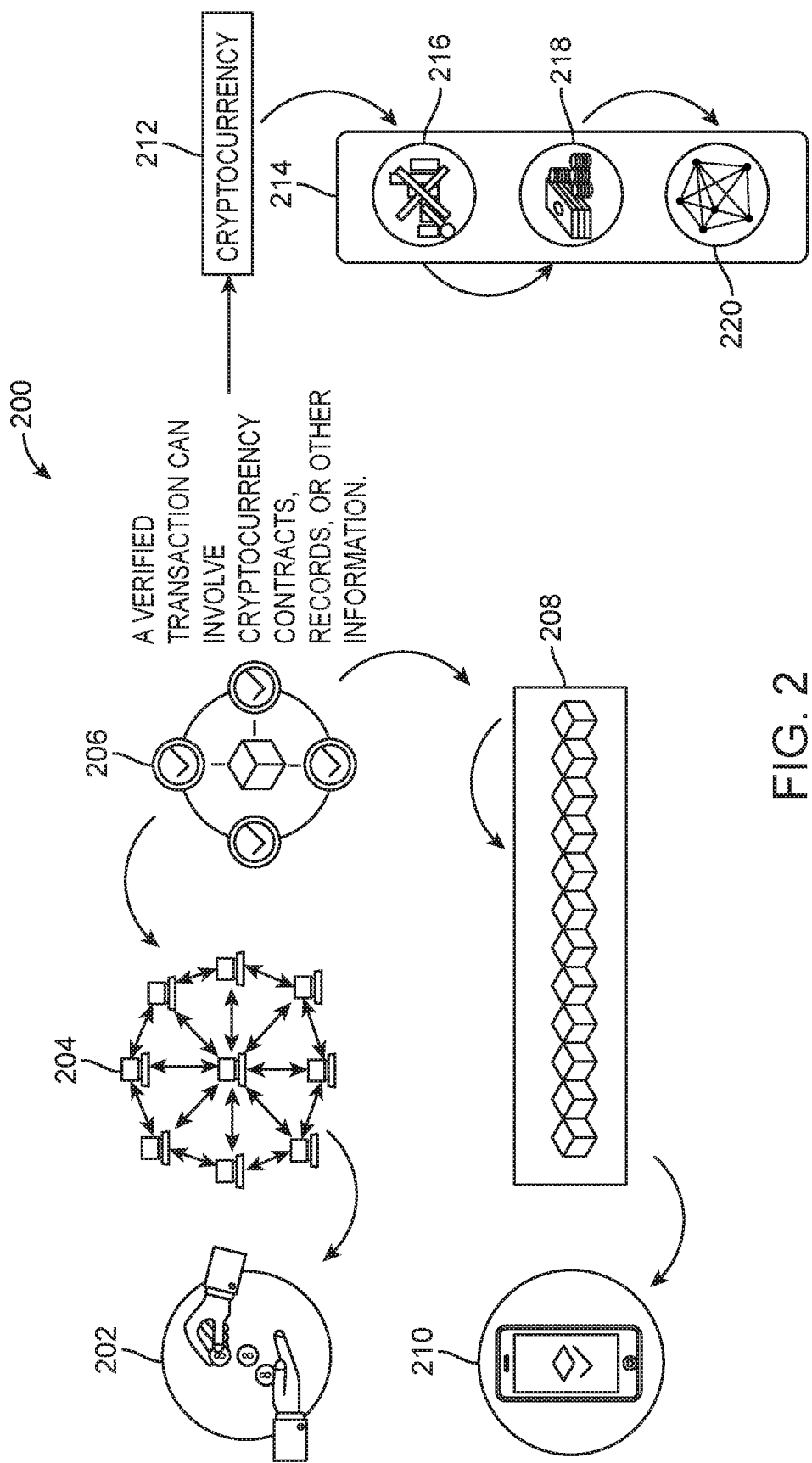
FIG. 2 illustrates an example blockchain network.

As the present technology utilizes the blockchain, FIG. 2 illustrates the basic blockchain elements. The blockchain is an incorruptible digital ledger of transactions that can be programmed to record not just financial transactions, but anything. As is shown in FIG. 2, first a transaction is requested 202. The requested transaction is broadcast to a peer-to-peer network consisting of computers or nodes 204. The network of nodes validates the transaction and the user status, using consensus algorithms. The algorithms of the present case enable the recordation of medical records according to a particular framework which protects patient privacy, but enables access to and updating of the medical records. The verified transaction 206 can also involve cryptocurrency, economic contracts, other types of records, or any other information. Once verified, the transaction is combined with other transactions to create a new block of data for the ledger 208. The new block is added to the existing blockchain, in a way that is permanent and unalterable and the transaction is complete 210.

In the cryptocurrency the example 212, the cryptocurrency 214 has no intrinsic value in that it is not redeemable for another commodity such as gold 216. The cryptocurrency has no physical form and exists only in the network 218. Finally, with cryptocurrency, its supply is not determined by a central bank and the network is completely decentralized 220. These features will also apply to the blockchain processing of medical records as disclosed herein.

In an alternate scenario, a, biometric numeric score can be generated from the group of biometric data types or subgroups of biometric data types. For example, iris data, and retina data could be used to generate a single biometric numeric score. The system could include grouping similar types of biometric data or disparate types of diet biometric data. For example, one group could be the voice recognition data, plus the DNA data, as disparate types of data. Another group could be facial recognition data and voice recognition data, combined to generate a biometric numeric score, that is recorded on the Blockchain. However, a preferred approach is to generate an individual biometric numeric score according to each respective biometric data type.

Figure 3:
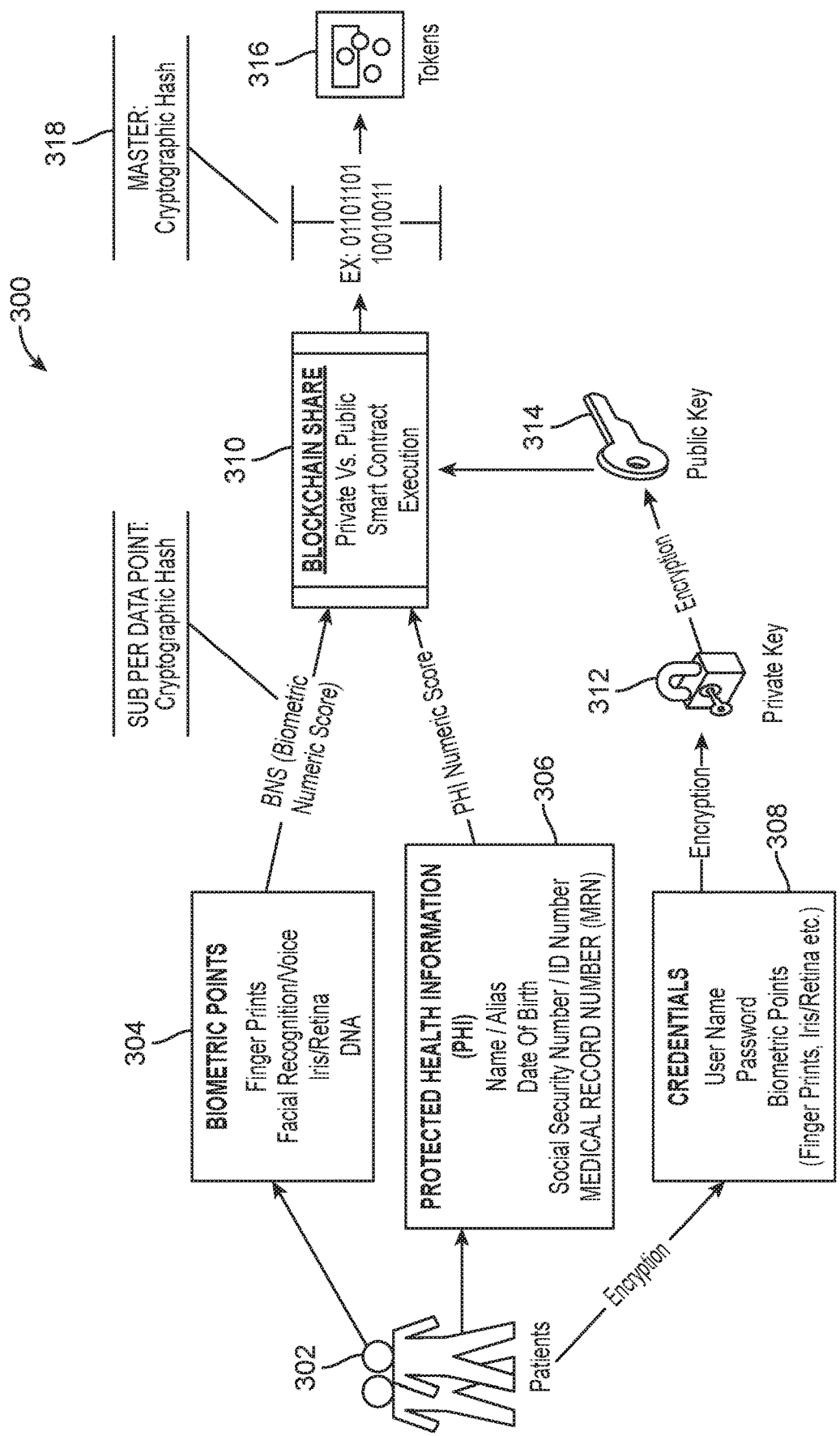
FIG. 3 illustrates an approach to utilizing a smart contract on a blockchain network to record patient data.

FIG. 3 illustrates some of the basic components of the framework 300 for recording patient medical information. The patient 302 has a number of different types of information which can be used to validate or identify that patient. The first type of data is biometric data 304. Biometric data can include fingerprints, facial recognition data, voice recognition data, iris data, retina data, and/or DNA. The framework disclosed herein includes generating, using a cryptographic hash, a, biometric numeric score (BNS) for each type of biometric data. This can be called a sub data point or sub data per data point. In other words, there is a cryptographic hash or biometric numeric score generated for fingerprints. There is a separate biometric numeric score or separate cryptographic hash generated for facial recognition data. This of course can include data identifying the physical or three-dimensional characteristics of a patient's face, which can then be used to validate that individual. There is a separate biometric numeric score or cryptographic hash generated for voice data for the patient. Furthermore, separate biometric numeric scores or cryptographic hashes are also generated for each of iris data, retina data, and DNA data. The biometric numeric scores are recorded on the Blockchain 310 which can be public or private in nature.

A smart contract 310 can be operable on the Blockchain network. The smart contract is essentially a set of instructions which are converted in the computer cord code stored and replicated on the Blockchain network such that its functions are supervised by the network of computers that run the Blockchain. The smart contract is programmed to perform functions according to the agreement and the Blockchain consensus algorithm automatically enforces the obligations. In the present scenario, a smart contract can be programmed and implemented on a Blockchain to perform the operations described herein with respect to implementing validation iterations different series of operations for validating the patient. In one example, the code for a smart contract can be written on the Ethereum Blockchain but they can be encoded on any Blockchain.

In addition to generating biometric numeric scores and recording the scores on a Blockchain network, the framework 300 also includes generating a protected health information (PHI) numeric score. In one aspect, a single PHI numeric score can be developed for all of the information such as one or more of the user name, an alias, a date of birth, a Social Security number, an ID number, or medical record number (MRN) 306. Other types of information can also apply, such as an address, previous addresses, previous aliases, passport numbers, or any other type of identification information for individual. Social networking data may also apply, such that information about social networking friends or family members, which can be included as part of protected health information for unification purposes. The single PHI numeric score is processed through a cryptographic hash and recorded on the Blockchain 310. In another example, individual PHI data types can be separately hashed or hashed according to groups of two or more types of information.

In another aspect, user credentials 308 are also received. The user credentials can be any one or more of a username, a password, a biometric data point such as a fingerprint, iris data, retina data, facial recognition data, and so forth. The credential data 308 is encrypted using first, a private key 312 followed by encryption using a public key 314 followed via recordation on the Blockchain network 310. Asymmetric cryptography, also known as public key cryptography, uses public and private keys to encrypt and decrypt data. The keys are simply large numbers that have been paired together, but are not identical (asymmetric). One key in the pair can be shared with everyone, which is the public key 314. The other key in the pair is kept secret and is the private key 312. Either of the keys can be used to encrypt a message. The opposite key from the one used to encrypt the message is used for decryption.

Digital signatures are based on asymmetric cryptography and can provide assurances of evidence to origin, identity and status of an electronic document, particularly health related documents as disclosed herein, as well as acknowledging informed consent by the signer. To create a digital signature, signing software (such as an email program) creates a one-way hash of the electronic data to be signed. The user's private key is then used to encrypt the hash, returning a value that is unique to the hashed data. The encrypted hash, along with other information such as the hashing algorithm, forms the digital signature. Any change in the data, even to a single bit, results in a different hash value. This attribute enables others to validate the integrity of the data by using the signer's public key to decrypt the hash. If the decrypted hash matches a second computed hash of the same data, it proves that the data hasn't changed since it was signed. If the two hashes don't match, the data has either been tampered with in some way (indicating a failure of integrity) or the signature was created with a private key that doesn't correspond to the public key presented by the signer (indicating a failure of authentication).

A digital signature also makes it difficult for the signing party to deny having signed something (the property of non-repudiation). If a signing party denies a valid digital signature, their private key has either been compromised, or they are being untruthful. Digital signatures can have the same legal weight as more traditional forms of signatures.

The data on the Blockchain 310 can also be used to generate a master cryptographic hash 318. From the master cryptographic hash, tokens can also be generated 316. The tokens in this context can be utilized in a health information Blockchain-based ecosystem in order to enable access to a patient's health data in one aspect or another. The following represents some basic example computer code written in Solidity and developed for generating tokens on the Ethereum blockchain. This code is only provided by way of example to understand how a blockchain-based token can be generated.

```
pragma solidity ^0.4.20;
contract MyToken {
  /* This creates an array with all balances */
  mapping (address=>uint256) public balanceOf;
  /* Initializes contract with initial supply tokens to the
     creator of the contract */
  function MyToken(
    uint256 initialSupply
  ) public {
    balanceOf[msg.sender]=initialSupply; //Give the creator all the initial tockens
  }
  /* Send coins */
  function transfer(address_to, uint256_value) public returns (bool success) {
    require(balanceOf[msg.sender]>, _value); //Check if the sender has enough
    require(balanceOf[_to]+_value>=balanceOf[_to]);
      //Check for overflows
    balanceOf[msg.sender]-=_value; //Subtract from the sender
    balanceOf[_to]+=_value; //Add the same to the recipient
    return true;
  }
}
```

Tokens, in this disclosure can relate to the ability as a bearer of a token to access personal health information for specific patient. An initial supply of tokens will be created and transferred, according to a smart contract to a wallet. The basic functionality of enabling how a transfer of tokens from one wallet to another can be programmed into the smart contract. Mechanisms for denying access to medical data or for destroying tokens will also be programmed. Different types of tokens can be generated with different permissions as well. For example, by generating a set of tokens associated with an individual patient's protected health information, the patient can provide tokens to various individuals. For example, an authorized doctor may have a fully authorized token which, when used, would enable access to their medical records. Tokens could be developed which would enable users access to anonymized health information for the purposes of medical studies. Tokens may be offered which advertisers or other entities may use to gain access to medical records, but which involve the payments to the patient. Thus, if an entity desires to do a study and requires the identity or certain amount of information associated with the patient, they could buy from the patient. The proper token type which enables the patient to receive income for their personal data also enables the entity to then "spend" those tokens by submitting them to the smart contract 310, which, according to this programming, would release the appropriate data of whatever varying scope (i.e., full data, anonymized data, data based on the patient as a youth, etc.) according to the respective token.

Thus, part of this disclosure involves receiving personal health information, biometric data, and credential data from a patient, processing, that data as described above for recordation on a Blockchain-based network. The method can include implanting a smart contract which will generate a group of tokens associated with the recorded patient information. The smart contract will also manage access to the patient health information by virtue of characteristics of tokens received from different entities from the group of tokens that were generated for the recorded patient information. The configuration of each token can include data that identifies its authorization to access that respective patient's information and what type of information is authorized to receive. For example, embedded within the token could be an identification that only anonymized patient information can be provided. The smart contract can respond to a request for that information as evidenced by the proper token and respond with anonymized information as requested. Tokens could be configured with such data as only being authorized to view medical information that is over five years old or only related to medical information between 2000 and 2005. In one aspect, entities, requesting a certain type of information could request the generation of tokens having particular characteristics. In such a case, the patient may receive a notification that certain types of tokens are being requested for a study or for advertising purposes, and so forth. A user interface could be presented in which the patient provides authorization through private key, biometric data, or credentials, which would authorize the generation of the requested token, perhaps for a fee.

Figure 4:
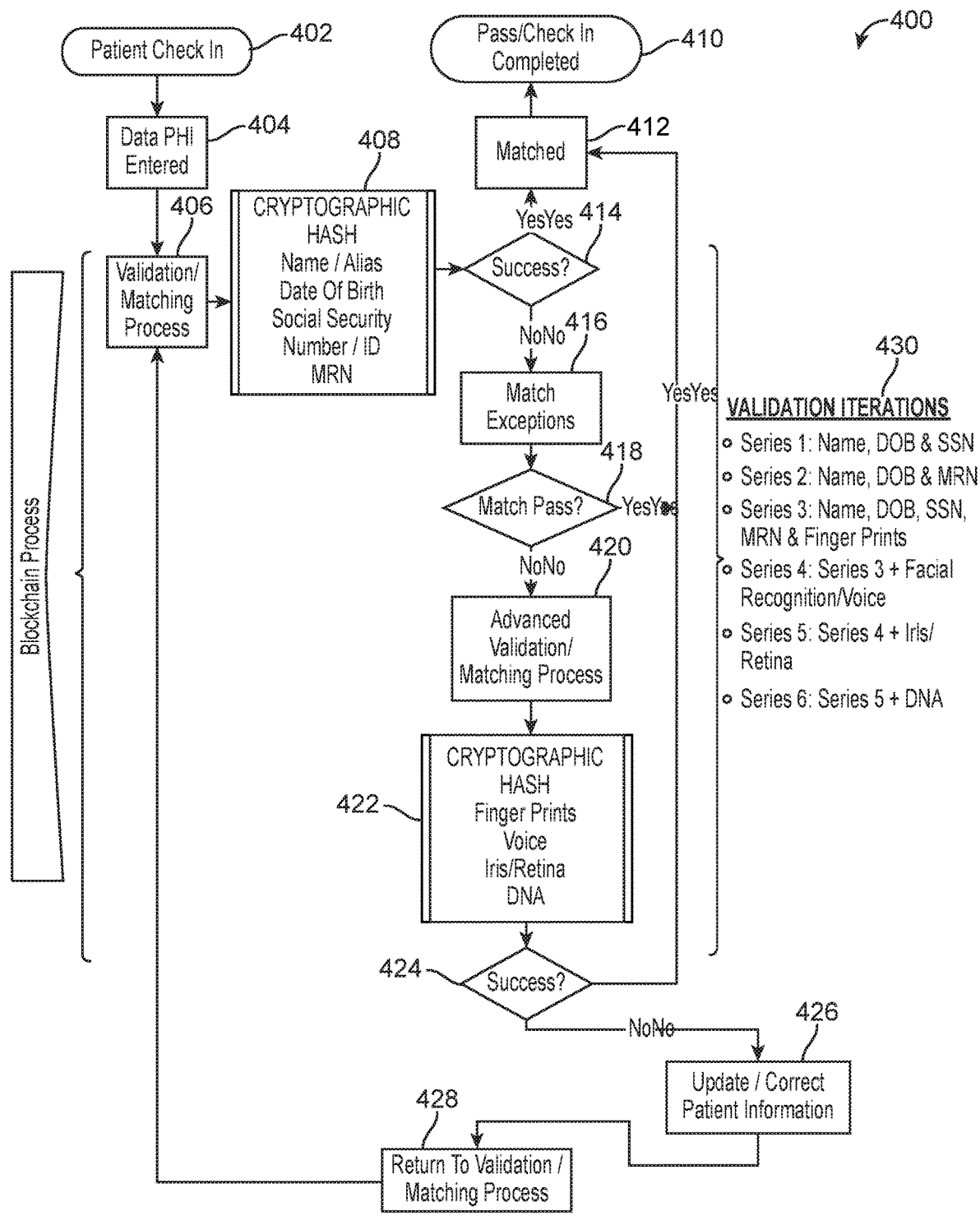
FIG. 4 illustrates a method aspect of this disclosure.

FIG. 4 illustrates an approach to the patient checking in to a system to receive access to patient information, including a process to validate the user. This process can also apply to any entity 402 seeking access to the data via the application of a token or credential.

The process 400 of FIG. 4 includes an entity checking in 402 and entering their PHI data 404. A user interface on a user client device can be used to access the smart contract which can execute the Blockchain process of validation and matching of the data to confirm access to patient information. The validation or matching process 406 can include performing a cryptographic hash 408 of the data entered by the entity such as name, alias, date of birth, Social Security number, ID number, or medical records number. Part of this disclosure is an iterative process of validation 430. A first iteration involves using the PHI data which is received from the entity 402. The first attempt or series 1 iteration 430 does not include any biometric data or data in which the biometric numeric score would need to be used. In one scenario, a successful outcome 414 of the cryptographic hash 408 indicates a match 412, which can thus complete or pass the entity as being able to access the medical records 410.

However, if the series 1 iteration is not successful 414, then a match exception process 416 can be initiated. In a series of iterations, different combinations of input can be considered as matches to enable the entity to have access. For example, a series 1 iteration can include the name, date of birth and Social Security number of the patient 430. If that is not successful, a series 2 iteration can include the name, date of birth and medical records number 430. The first group of iterations does not include biometric data at this stage, but a varying list of non-biometric data is tested. Other variations or groupings of nonbiometric data can be provided in one or more series. If there is a match pass 418, the flow proceeds to confirm the match 412 and completes the check in 410.

However, if there is not a match pass 418, then additional iterations are applied which iteratively increase the type of information and begins to include incrementally biometric data. For example, a series 3 iteration can include a name, date of birth, Social Security number, medical records number, and fingerprint data. In this scenario, the system performs a match against the sub data points in the biometric numeric scores. The process can include a cryptographic hash PHI match, along with the biometric numeric score hash for a specific subtype of biometric data, such as the fingerprint data only. In this scenario, other types of biometric data would not be matched. In this scenario, the generation of separate biometric numeric scores for each sub biometric data type enables an iterative process to access Blockchain-based data in which the subtype of data can be separately accessed. This involves an advanced validation or matching process 420 which can include both non-biometric data as well as biometric data.

A series 4 iteration can include all of the data in a series 3 iteration +1 or more of facial recognition data, and/or voice recognition data. A fifth series can include all of the data in series 4 +1 or more of Iris data and/or retina data for the patient. Finally, a $6^{th}$ series 430 can include all of the data in series 5 plus DNA data. As can be appreciated, an important aspect of this disclosure includes the particular framework or pattern of iterating over the various types of data (biometric, nonbiometric, etc.) that is recorded on the Blockchain in order to complete a check in process, or to pass an individual to gain access to medical records. As biometric data begins to be used, a cryptographic hash is generated to match with data points on the Blockchain 422 on a sub data type basis. Again, the sub data type means that there is a cryptographic hash or biometric numeric score for each. Biometric data type, such as fingerprint, facial recognition, voice recognition, iris data, retina data, and/or DNA. Other biometric type data could also be considered.

Based on a consideration of any one or more of the series of validation iterations, the system could indicate success 424 of the validation process which would bring the flow to the matched confirmation stage 412, and thus complete the check-in.

Where the matching process is a failure, the system could then engage in an interaction with the patient to update or correct the patient information 426 and then cause the system to return to the validation or matching process 428, which is shown in block 406.

The process outlined in FIG. 4 is implemented by a smart contract on the Blockchain network. The user interface enables the entity 402 to enter nonbiometric personal data to seek access to the medical records and, where necessary, includes the components (input components 145) which can enable the system to receive biometric data, such as a fingerprint reader, a facial recognition scanner or sensing device, a component which can receive a voiceprint, or voice data of the user, an iris detection unit, a retina detection unit, or a DNA acceptance or receptive unit. In one aspect, these various components could be built into a client device, such as a mobile phone, which enables a fingerprint reception, a face print, as well as other biometric identification data. In another aspect, the patient 402 may be at a hospital where there is a kiosk or a computing device which enables the receipt and processing of the various types of biometric data.

Figure 5:
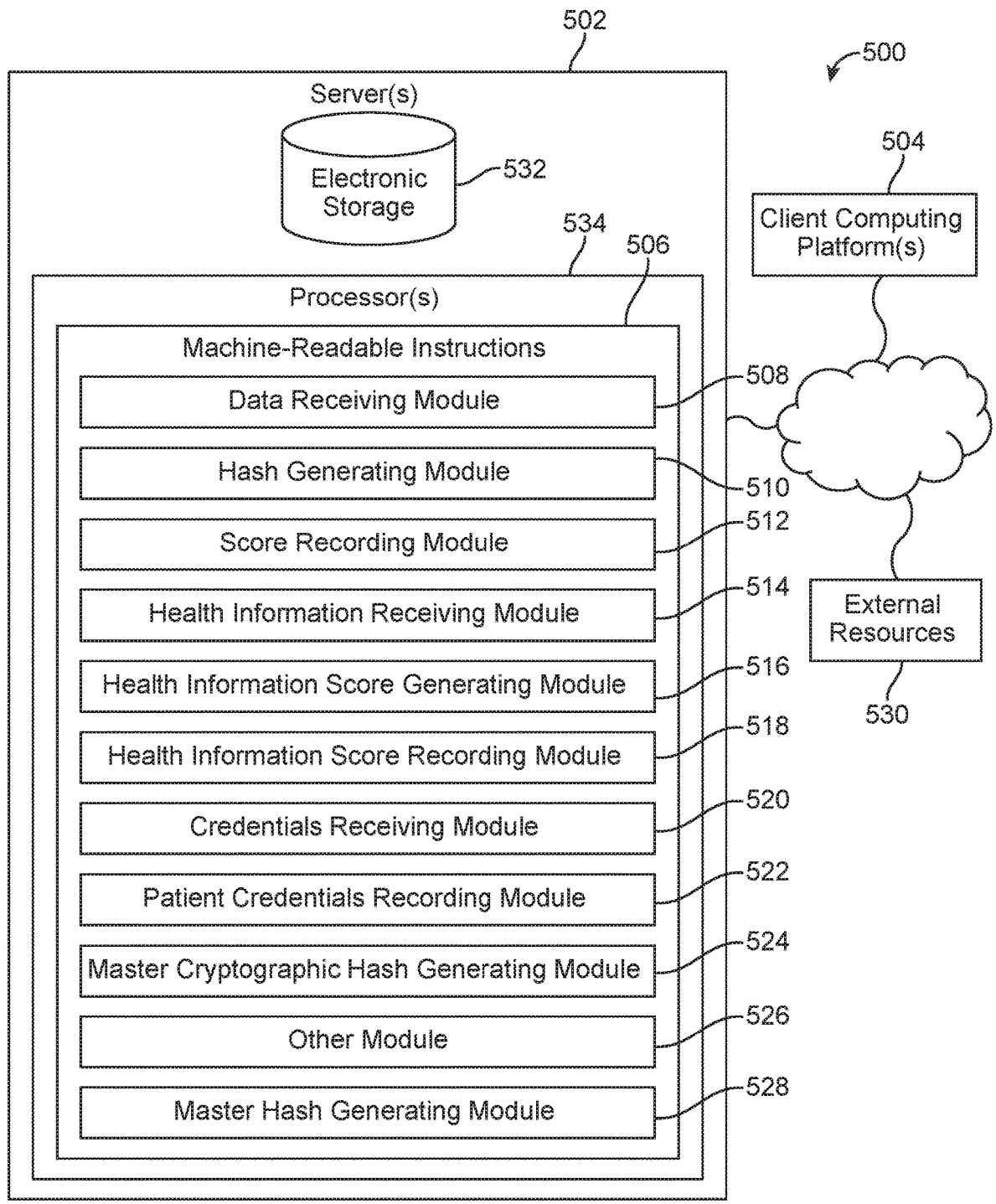
FIG. 5 illustrates a system embodiment.

FIG. 5 illustrates a system 500, in accordance with one or more implementations. In some implementations, system 500 may include one or more servers 502. Server(s) 502 may be configured to communicate with one or more client computing platforms 504 according to a client/server architecture and/or other architectures. Client computing platform(s) 504 may be configured to communicate with other client computing platforms via server(s) 502 and/or according to a peer-to-peer architecture and/or other architectures. Users may access system 500 via client computing platform(s) 504.

Server(s) 502 may be configured by machine-readable instructions 506. Machine-readable instructions 506 may include one or more instruction modules. The instruction modules may include computer program modules. The instruction modules may include one or more of a data receiving module 508, a hash generating module 510, a score recording module 512, a health information receiving module 514, a health information score generating module 516, a health information score recording module 518, a credentials receiving module 520, a patient credentials recording module 522, a master cryptographic hash generating module 524, another module 526, a master hash generating module 528, and/or other instruction modules.

Data receiving module 508 may be configured to receive, from a patient, first biometric data associated with a first biometric data type and second biometric data associated with a second biometric data type. Upon a successful match to validate the patient, the method further includes updating or correcting patient information.

Hash generating module 510 may be configured to generate a cryptographic hash of the first biometric data and the second biometric data to yield a biometric numeric score.

Score recording module 512 may be configured to record the biometric numeric score on a blockchain network to yield a recorded biometric numeric score.

Health information receiving module 514 may be configured to receive protected health information for the patient.

Health information score generating module 516 may be configured to generate a protected health information numeric score based on the protected health information for the patient.

Health information score recording module 518 may be configured to record the protected health information numeric score on the blockchain network to yield a recorded protected health information numeric score.

Credentials receiving module 520 may be configured to receive and encrypting patient credentials to yield encrypted patient credentials.

Patient credentials recording module 522 may be configured to record the encrypted patient credentials on the blockchain network to yield recorded encrypted patient credentials.

Master cryptographic hash generating module 524 may be configured to generate a master cryptographic hash based at least in part on the recorded biometric numeric score. By way of a non-limiting example, this may be recorded protected health information, numeric score, and the recorded encrypted patient credentials. By way of a non-limiting example, the protected health information may include one or more of a name of the patient, a date of birth of the patient, a social security number of the patient (or other number identifying the user) and a medical record number of the patient. Validating the patient may include when a validation process associated with the protected health information is not successful, determining a match by determining whether a cryptographic hash match exists for any of the first biometric data or separately with the second biometric data.

A validation module 526 may be configured to validate via a validation module, including a smart contract operating on the blockchain network. By way of a non-limiting example, the patient may use the master cryptographic hash and may be based on a series of validation iterations including a first series of validation iterations limited to the protected health information and a second series of validation iterations including the protected health information and one or more biometric data types. Validating the patient may further include applying the first series of validation iterations. By way of a non-limiting example, the first series of validation iterations may include a first validation iteration receiving only a name, a date of birth, and a social security number of the patient and wherein a second validation iteration includes receiving only the name, the date of birth, and a medical record number associated with the patient. Validating the patient may further include applying the second series of validation iterations.

By way of non-limiting example, the second series of validation iterations may include a third validation iteration which includes receiving only the name, the date of birth, the social security number, the medical number, and the fingerprint. A fourth validation iteration include receiving only the name, the date of birth, the social security number, the medical record number, the fingerprint, and one of facial data or voice data of the patient. By way of non-limiting example, a fifth validation iteration may include receiving only the name, the date of birth, the social security number, the medical record number, the fingerprint, one of the facial data or the voice data, and an iris/retina recognition of the patient. By way of non-limiting example, a sixth validation iteration may include receiving only the name, the date of birth, the social security number, the medical record number, the fingerprint, one of the facial data or the voice data, an iris/retina recognition of the patient and DNA data may be associated with the patient.

Master hash generating module 528 may be configured to generate tokens associated with the master cryptographic hash. The tokens can be used to gain access to health information associated with the patient.

Tokens in this context can be a special kind of virtual currency that reside on their own blockchains and represent an asset or utility such as the utility of accessing health care information. For example, an individual can have a crypto token that represents x number of customer loyalty points on a blockchain that is used to manage such details for a retail chain. There can be another crypto token that gives entitlement to the token holder to view medical records for an individual associated with the token. Such crypto tokens are tradable and transferrable among the various participants of the blockchain.

Such crypto tokens often serve as the transaction units on the blockchains that are created using the standard templates like that of Ethereum network that allows a user to create his/her own tokens, as is disclosed herein. Such blockchains work on the concept of smart contracts or decentralized applications, where the programmable, self-executing code is used to process and manage the various transactions occurring on the blockchain.

The tokens disclosed herein can be specific virtual currencies that have their own dedicated blockchains and are primarily used as a medium for digital payments or as a medium for accessing medical record information. In another aspect, the crypto tokens can operate on top of a blockchain and can act as a medium for creation and execution of decentralized apps and smart contracts, and the tokens are used to facilitate the transactions, particularly for accessing medical record data as disclosed herein. Tokens are usually created, distributed, sold and circulated through the standard initial coin offering (ICO) process that involves a crowdfunding exercise to fund project development. In this case the tokens can be created in an ICO or as users register their medical record information with the system, or based on some other mechanism.

In some implementations, server(s) 502, client computing platform(s) 504, and/or external resources 530 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 502, client computing platform(s) 504, and/or external resources 530 may be operatively linked via some other communication media.

A given client computing platform 504 may include one or more processors configured to execute computer program modules. The computer program modules may be configured to enable an expert or user associated with the given client computing platform 504 to interface with system 500 and/or external resources 530, and/or provide other functionality attributed herein to client computing platform(s) 504. By way of non-limiting example, the given client computing platform 504 may include one or more of a desktop computer, a laptop computer, a handheld computer, a tablet computing platform, a notebook, a Smartphone, a gaming console, and/or other computing platforms.

External resources 530 may include sources of information outside of system 500, external entities participating with system 500, and/or other resources. In some implementations, some or all of the functionality attributed herein to external resources 530 may be provided by resources included in system 500.

Server(s) 502 may include electronic storage 532, one or more processors 534, and/or other components. Server(s) 502 may include communication lines, or ports to enable the exchange of information with a network and/or other computing platforms. Illustration of server(s) 502 in FIG. 5 is not intended to be limiting. Server(s) 502 may include a plurality of hardware, software, and/or firmware components operating together to provide the functionality attributed herein to server(s) 502. For example, server(s) 502 may be implemented by a cloud of computing platforms operating together as server(s) 502.

Electronic storage 532 may comprise non-transitory storage media that electronically stores information. The electronic storage media of electronic storage 532 may include one or both of system storage that is provided integrally (i.e., substantially non-removable) with server(s) 502 and/or removable storage that is removably connectable to server(s) 502 via, for example, a port (e.g., a USB port, a firewire port, etc.) or a drive (e.g., a disk drive, etc.). Electronic storage 532 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 532 may include one or more virtual storage resources (e.g., cloud storage, a virtual private network, and/or other virtual storage resources). Electronic storage 532 may store software algorithms, information determined by processor(s) 534, information received from server(s) 502, information received from client computing platform(s) 504, and/or other information that enables server(s) 502 to function as described herein.

Processor(s) 534 may be configured to provide information processing capabilities in server(s) 502. As such, processor(s) 534 may include one or more of a digital processor, an analog processor, a digital circuit designed to process information, an analog circuit designed to process information, a state machine, and/or other mechanisms for electronically processing information. Although processor(s) 534 is shown in FIG. 5 as a single entity, this is for illustrative purposes only. In some implementations, processor(s) 534 may include a plurality of processing units. These processing units may be physically located within the same device, or processor(s) 534 may represent processing functionality of a plurality of devices operating in coordination. Processor(s) 534 may be configured to execute modules 508, 510, 512, 514, 516, 518, 520, 522, 524, 526, and/or 528, and/or other modules. Processor(s) 534 may be configured to execute modules 508, 510, 512, 514, 516, 518, 520, 522, 524, 526, and/or 528, and/or other modules by software; hardware; firmware; some combination of software, hardware, and/or firmware; and/or other mechanisms for configuring processing capabilities on processor(s) 534. As used herein, the term "module" may refer to any component or set of components that perform the functionality attributed to the module. This may include one or more physical processors during execution of processor readable instructions, the processor readable instructions, circuitry, hardware, storage media, or any other components.

It should be appreciated that although modules 508, 510, 512, 514, 516, 518, 520, 522, 524, 526, and/or 528 are illustrated in FIG. 5 as being implemented within a single processing unit, in implementations in which processor(s) 534 includes multiple processing units, one or more of modules 508, 510, 512, 514, 516, 518, 520, 522, 524, 526, and/or 528 may be implemented remotely from the other modules. The description of the functionality provided by the different modules 508, 510, 512, 514, 516, 518, 520, 522, 524, 526, and/or 528 described below is for illustrative purposes, and is not intended to be limiting, as any of modules 508, 510, 512, 514, 516, 518, 520, 522, 524, 526, and/or 528 may provide more or less functionality than is described. For example, one or more of modules 508, 510, 512, 514, 516, 518, 520, 522, 524, 526, and/or 528 may be eliminated, and some or all of its functionality may be provided by other ones of modules 508, 510, 512, 514, 516, 518, 520, 522, 524, 526, and/or 528. As another example, processor(s) 534 may be configured to execute one or more additional modules that may perform some or all of the functionality attributed below to one of modules 508, 510, 512, 514, 516, 518, 520, 522, 524, 526, and/or 528.

Figure 6:
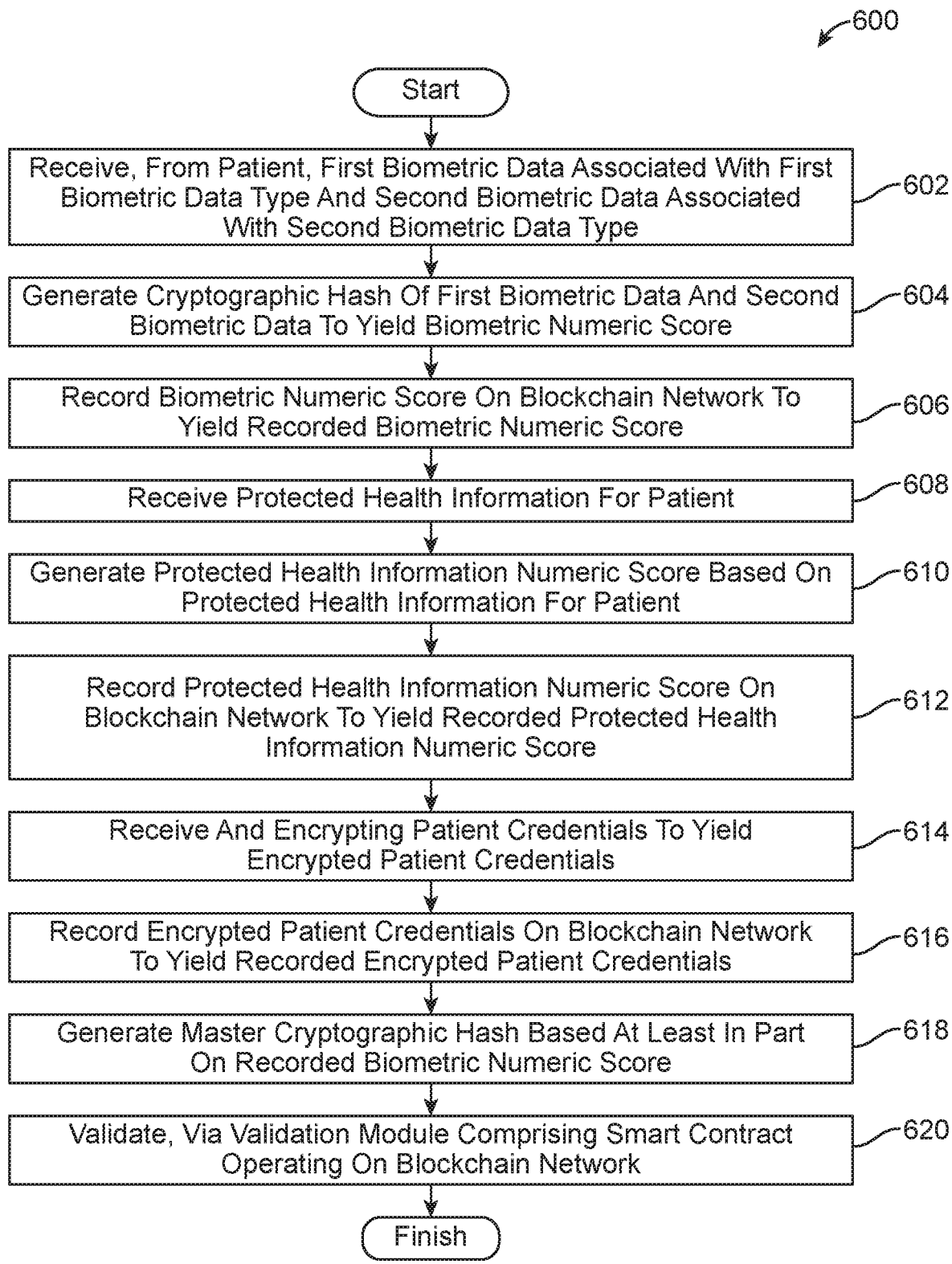
FIG. 6 illustrates a method embodiment.

FIG. 6 illustrates a method 600 for processing protected health information of a user, in accordance with one or more implementations. The operations of method 600 presented below are intended to be illustrative. In some implementations, method 600 may be accomplished with one or more additional operations not described, and/or without one or more of the operations discussed. Additionally, the order in which the operations of method 600 are illustrated in FIG. 6 and described below is not intended to be limiting.

In some implementations, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

FIG. 6 illustrates method 600, in accordance with one or more implementations.

An operation 602 may include receiving, from a patient, first biometric data associated with a first biometric data type and second biometric data associated with a second biometric data type. Operation 602 may be performed by one or more hardware processors configured by machine-readable instructions including a module that is the same as or similar to data receiving module 108, in accordance with one or more implementations.

An operation 604 may include generating a cryptographic hash of the first biometric data and the second biometric data to yield a biometric numeric score. Operation 604 may be performed by one or more hardware processors configured by machine-readable instructions including a module that is the same as or similar to hash generating module 510, in accordance with one or more implementations.

An operation 606 may include recording the biometric numeric score on a blockchain network to yield a recorded biometric numeric score. Operation 606 may be performed by one or more hardware processors configured by machine-readable instructions including a module that is the same as or similar to score recording module 512, in accordance with one or more implementations.

An operation 608 may include receiving protected health information for the patient. Operation 608 may be performed by one or more hardware processors configured by machine-readable instructions including a module that is the same as or similar to health information receiving module 514, in accordance with one or more implementations.

An operation 610 may include generating a protected health information numeric score based on the protected health information for the patient. Operation 610 may be performed by one or more hardware processors configured by machine-readable instructions including a module that is the same as or similar to health information score generating module 516, in accordance with one or more implementations.

An operation 612 may include recording the protected health information numeric score on the blockchain network to yield a recorded protected health information numeric score. Operation 612 may be performed by one or more hardware processors configured by machine-readable instructions including a module that is the same as or similar to health information score recording module 518, in accordance with one or more implementations.

An operation 614 may include receiving and encrypting patient credentials to yield encrypted patient credentials. Operation 614 may be performed by one or more hardware processors configured by machine-readable instructions including a module that is the same as or similar to credentials receiving module 520, in accordance with one or more implementations.

An operation 616 may include recording the encrypted patient credentials on the blockchain network to yield recorded encrypted patient credentials. Operation 616 may be performed by one or more hardware processors configured by machine-readable instructions including a module that is the same as or similar to patient credentials recording module 522, in accordance with one or more implementations.

An operation 618 may include generating a master cryptographic hash based at least in part on the recorded biometric numeric score. The may be recorded protected health information, numeric score, and the recorded encrypted patient credentials. Operation 618 may be performed by one or more hardware processors configured by machine-readable instructions including a module that is the same as or similar to master cryptographic hash generating module 524, in accordance with one or more implementations.

An operation 620 may include validating, via a validation module including a smart contract operating on the blockchain network. The patient by may use the master cryptographic hash, and based on a series of validation iterations including a first series of validation iterations limited to the protected health information, and a second series of validation iterations including the protected health information and one or more biometric data types. Operation 620 may be performed by one or more hardware processors configured by machine-readable instructions including a module that is the same as or similar to an other module 526, including a validation module, in accordance with one or more implementations.

The method can also include generating tokens associated with the master cryptographic hash. A generation operation may be performed by one or more hardware processors configured by machine-readable instructions including a module that is the same as or similar to master hash generating module 528, in accordance with one or more implementations.

Figure 7:
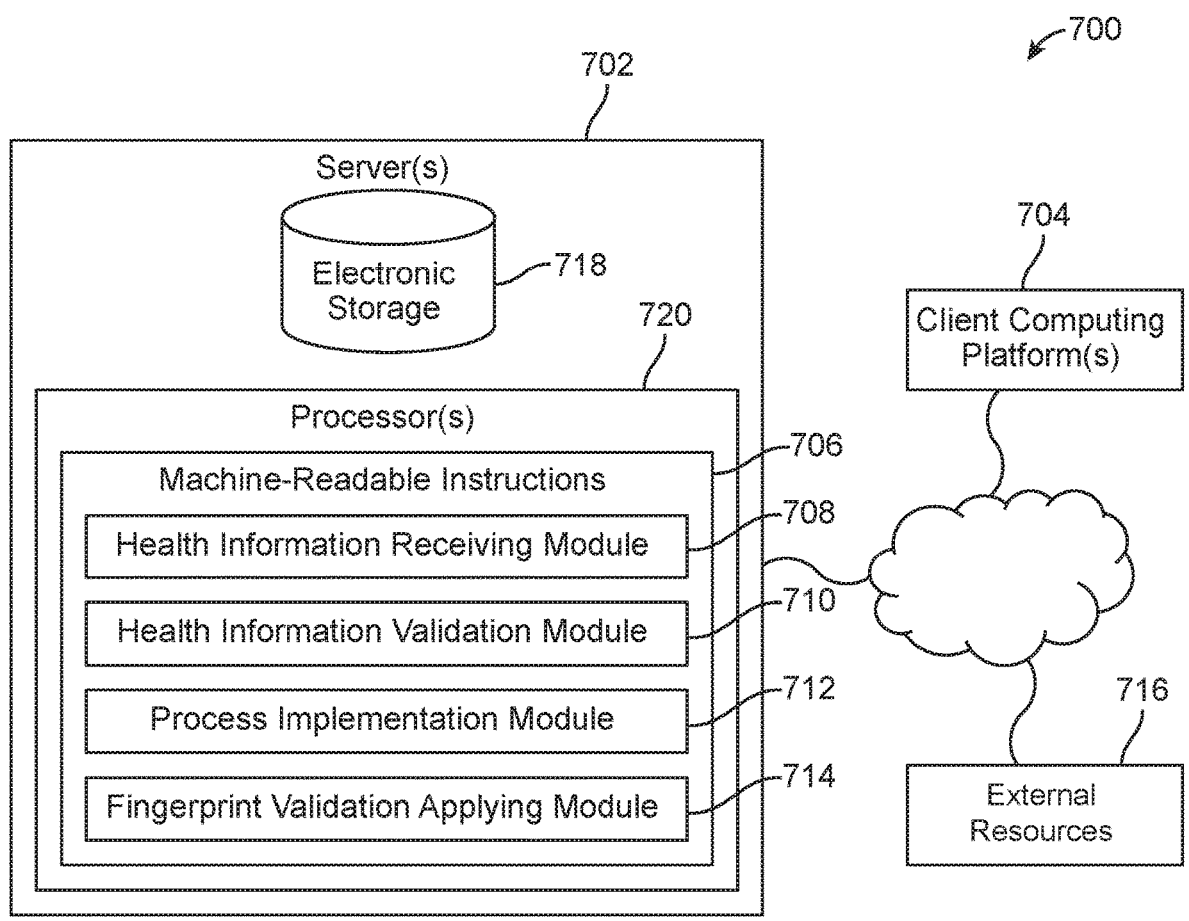
FIG. 7 illustrates another system.

FIG. 7 illustrates a system 700, in accordance with one or more implementations. In some implementations, system 700 may include one or more servers 702. Server(s) 702 may be configured to communicate with one or more client computing platforms 704 according to a client/server architecture and/or other architectures. Client computing platform(s) 704 may be configured to communicate with other client computing platforms via server(s) 702 and/or according to a peer-to-peer architecture and/or other architectures. Users may access system 700 via client computing platform(s) 704.

Server(s) 702 may be configured by machine-readable instructions 706. Machine-readable instructions 706 may include one or more instruction modules. The instruction modules may include computer program modules. The instruction modules may include one or more of a health information receiving module 708, a health information validation module 710, a process implementation module 712, a fingerprint validation applying module 714, and/or other instruction modules.

Health information receiving module 708 may be configured to receive personal health information associated with a patient to be validated in a medical record system.

Health information validation module 710 may be configured to validate the personal health information of the patient by determining whether a match exists with a cryptographic hash of previously entered personal health information of patients. The cryptographic hash may be recorded on a blockchain network. Each respective type of biometric data may be separately cryptographically hashed to generate a respective biometric numeric score for the respective type of biometric data and which is recorded on the blockchain network. Of course an alpha-numeric score or a pure alphabet based score could be used as well.

Process implementation module 712 may be configured to, when a match exception exists based on the personal health information of the patient, implement a process of validation iterations which includes determining a match of received biometric data from the patient against a cryptographic hash of a biometric numeric score recorded on the blockchain network. The received biometric data may include a first type of biometric data. The biometric numeric score may represent a first biometric score recorded on the blockchain network for the first type of biometric data. The process of validation iterations may include iteratively matching respective received biometric data from the patient of a respective type of biometric data. By way of non-limiting example, the first type of biometric data may include a fingerprint, a second type of biometric data includes one of facial data and/or voice data, a third type of biometric data includes iris data and/or retina image data, and a fourth type of biometric data includes DNA data of the patient.

The process of validation iterations may further include an ordered series of validation matching operations including applying a fingerprint validation. The biometric numeric score may represent a sub data point representing a type of biometric data used to validate the patient.

Fingerprint validation applying module 714 may be configured to apply the fingerprint validation plus a facial data validation or a voice data validation, applying the fingerprint validation, one of the facial data validation or the voice data validation, and an iris validation or a retina scan validation and applying a DNA validation process for the patient.

In some implementations, server(s) 702, client computing platform(s) 704, and/or external resources 716 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 702, client computing platform(s) 704, and/or external resources 716 may be operatively linked via some other communication media.

A given client computing platform 704 may include one or more processors configured to execute computer program modules. The computer program modules may be configured to enable an expert or user associated with the given client computing platform 704 to interface with system 700 and/or external resources 716, and/or provide other functionality attributed herein to client computing platform(s) 704. By way of non-limiting example, the given client computing platform 704 may include one or more of a desktop computer, a laptop computer, a handheld computer, a tablet computing platform, a notebook, a Smartphone, a gaming console, and/or other computing platforms.

External resources 716 may include sources of information outside of system 700, external entities participating with system 700, and/or other resources. In some implementations, some or all of the functionality attributed herein to external resources 716 may be provided by resources included in system 700.

Server(s) 702 may include electronic storage 718, one or more processors 720, and/or other components. Server(s) 702 may include communication lines, or ports to enable the exchange of information with a network and/or other computing platforms. Illustration of server(s) 702 in FIG. 7 is not intended to be limiting. Server(s) 702 may include a plurality of hardware, software, and/or firmware components operating together to provide the functionality attributed herein to server(s) 702. For example, server(s) 702 may be implemented by a cloud of computing platforms operating together as server(s) 702.

Electronic storage 718 may comprise non-transitory storage media that electronically stores information. The electronic storage media of electronic storage 718 may include one or both of system storage that is provided integrally (i.e., substantially non-removable) with server(s) 702 and/or removable storage that is removably connectable to server(s) 702 via, for example, a port (e.g., a USB port, a firewire port, etc.) or a drive (e.g., a disk drive, etc.). Electronic storage 718 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 718 may include one or more virtual storage resources (e.g., cloud storage, a virtual private network, and/or other virtual storage resources). Electronic storage 718 may store software algorithms, information determined by processor(s) 720, information received from server(s) 702, information received from client computing platform(s) 704, and/or other information that enables server(s) 702 to function as described herein.

Processor(s) 720 may be configured to provide information processing capabilities in server(s) 702. As such, processor(s) 720 may include one or more of a digital processor, an analog processor, a digital circuit designed to process information, an analog circuit designed to process information, a state machine, and/or other mechanisms for electronically processing information. Although processor(s) 720 is shown in FIG. 7 as a single entity, this is for illustrative purposes only. In some implementations, processor(s) 720 may include a plurality of processing units. These processing units may be physically located within the same device, or processor(s) 720 may represent processing functionality of a plurality of devices operating in coordination. Processor(s) 720 may be configured to execute modules 708, 710, 712, and/or 714, and/or other modules. Processor(s) 720 may be configured to execute modules 708, 710, 712, and/or 714, and/or other modules by software; hardware; firmware; some combination of software, hardware, and/or firmware; and/or other mechanisms for configuring processing capabilities on processor(s) 720. As used herein, the term "module" may refer to any component or set of components that perform the functionality attributed to the module. This may include one or more physical processors during execution of processor readable instructions, the processor readable instructions, circuitry, hardware, storage media, or any other components.

It should be appreciated that although modules 708, 710, 712, and/or 714 are illustrated in FIG. 7 as being implemented within a single processing unit, in implementations in which processor(s) 720 includes multiple processing units, one or more of modules 708, 710, 712, and/or 714 may be implemented remotely from the other modules. The description of the functionality provided by the different modules 708, 710, 712, and/or 714 described below is for illustrative purposes, and is not intended to be limiting, as any of modules 708, 710, 712, and/or 714 may provide more or less functionality than is described. For example, one or more of modules 708, 710, 712, and/or 714 may be eliminated, and some or all of its functionality may be provided by other modules 708, 710, 712, and/or 714. As another example, processor(s) 720 may be configured to execute one or more additional modules that may perform some or all of the functionality attributed below to one of modules 708, 710, 712, and/or 714.

Figure 8:
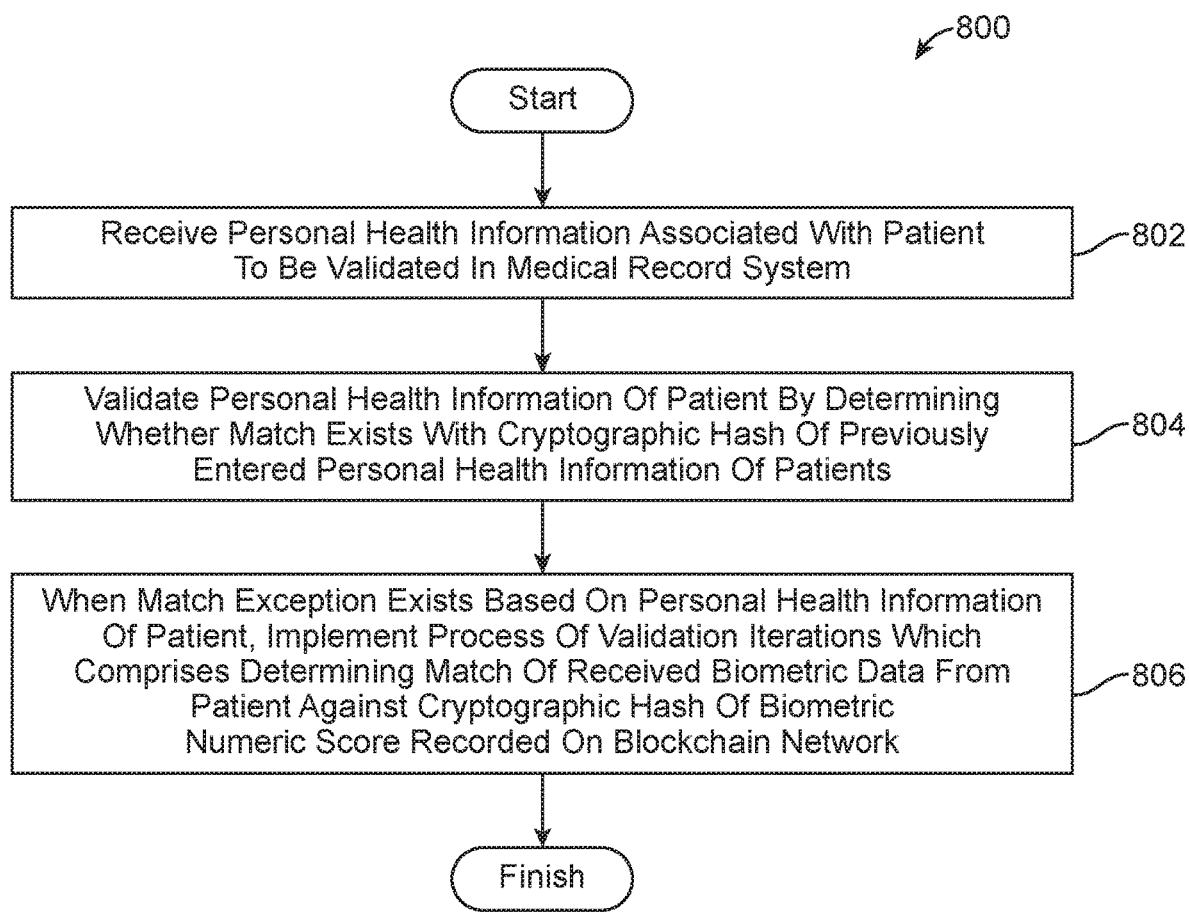
FIG. 8 illustrates another method embodiment.

FIG. 8 is a method 800 for matching data and when and how to implement an iterative validation process, in accordance with one or more implementations. The operations of method 800 presented below are intended to be illustrative. In some implementations, method 800 may be accomplished with one or more additional operations not described, and/or without one or more of the operations discussed. Additionally, the order in which the operations of method 800 are illustrated in FIG. 8 and described below is not intended to be limiting.

In some implementations, method 800 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 800 in response to instructions stored electronically on an electronic storage medium. The one or more processing devices may include one or more devices configured through hardware, firmware, and/or software to be specifically designed for execution of one or more of the operations of method 800.

FIG. 8 illustrates method 800, in accordance with one or more implementations. An operation 802 may include receiving personal health information associated with a patient to be validated in a medical record system. Operation 802 may be performed by one or more hardware processors configured by machine-readable instructions including a module that is the same as or similar to health information receiving module 708, in accordance with one or more implementations.

An operation 804 may include validating the personal health information of the patient by determining whether a match exists with a cryptographic hash of previously entered personal health information of patients. The cryptographic hash may be recorded on a blockchain network. Operation 804 may be performed by one or more hardware processors configured by machine-readable instructions including a module that is the same as or similar to health information validation module 710, in accordance with one or more implementations.

An operation 806 may include when a match exception exists based on the personal health information of the patient, implementing a process of validation iterations which includes determining a match of received biometric data from the patient against a cryptographic hash of a biometric numeric score recorded on the blockchain network. The biometric numeric score may represent a sub data point representing a type of biometric data used to validate the patient. Operation 806 may be performed by one or more hardware processors configured by machine-readable instructions including a module that is the same as or similar to process implementation module 712, in accordance with one or more implementations.

The method can also include applying the fingerprint validation plus a facial data validation or a voice data validation, applying the fingerprint validation, one of the facial data validation or the voice data validation, and an iris validation or a retina scan validation and applying a DNA validation process for the patient. This operation may be performed by one or more hardware processors configured by machine-readable instructions including a module that is the same as or similar to fingerprint validation applying module 714, in accordance with one or more implementations.

It is further contemplated that there can be many other uses and/or applications associated with the various embodiments of the present disclosure that a person having ordinary skill in the art would recognize.

As discussed above, the various embodiments can be implemented in a wide variety of operating environments, which in some cases can include one or more user computers, computing devices, or processing devices which can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Various aspects also can be implemented as part of at least one service or Web service, such as may be part of a service-oriented architecture. Services such as Web services can communicate using any appropriate type of messaging, such as by using messages in extensible markup language (XML) format and exchanged using an appropriate protocol such as SOAP (derived from the "Simple Object Access Protocol"). Processes provided or executed by such services can be written in any appropriate language, such as the Web Services Description Language (WSDL). Using a language such as WSDL allows for functionality such as the automated generation of client-side code in various SOAP frameworks.

Most embodiments utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a Web server, the Web server can run any of a variety of server or mid-tier applications, including HTTP servers, FTP servers, CGI servers, data servers, Java servers, and business application servers. The server(s) also may be capable of executing programs or scripts in response requests from user devices, such as by executing one or more Web applications that may be implemented as one or more scripts or programs written in any programming language, such as Java®, C, C# or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:
1. A method comprising:
receiving, from a patient, first biometric data associated with a first biometric data type and second biometric data associated with a second biometric data type, wherein the first biometric data type differs from the second biometric data type;
generating a cryptographic hash of the first biometric data and the second biometric data to yield a biometric numeric score;

recording the biometric numeric score on a blockchain network to yield a recorded biometric numeric score, wherein the blockchain network comprises a plurality of nodes each running a consensus algorithm to confirm the recorded biometric numeric score being recorded in a distributed ledger across the plurality of nodes;

receiving protected health information for the patient;

generating a protected health information numeric score based on the protected health information for the patient;

recording the protected health information numeric score on the blockchain network to yield a recorded protected health information numeric score;

receiving and encrypting patient credentials to yield encrypted patient credentials;

recording the encrypted patient credentials on the blockchain network to yield recorded encrypted patient credentials;

generating a master cryptographic hash based at least in part on the recorded biometric numeric score, the recorded protected health information and the recorded encrypted patient credentials; and validating, via the blockchain network operating a validation smart contract and upon a request for validation by one of the patient or another person, the patient by using the master cryptographic hash, and based on the smart contract on the blockchain network performing a series of validation iterations comprising a first series of validation iterations limited to the protected health information, and a second series of validation iterations comprising the protected health information and one or more biometric data types.

2. The method of claim 1, further comprising generating tokens associated with the master cryptographic hash.

3. The method of claim 2, wherein the tokens can be used to gain access to health information associated with the patient.

4. The method of claim 1, wherein the protected health information comprises one or more of a name of the patient, a date of birth of the patient, a social security number of the patient and a medical record number of the patient.

5. The method of claim 1, wherein validating the patient further comprises applying the first series of validation iterations, wherein the first series of validation iterations comprises a first validation iteration comprising receiving only a name, a date of birth, and a social security number of the patient and wherein a second validation iteration comprises receiving only the name, the date of birth, and a medical record number associated with the patient.

6. The method of claim 5, wherein validating the patient further comprises applying the second series of validation iterations, wherein the second series of validation iterations comprises a third validation iteration comprising receiving only the name, the date of birth, the social security number, the medical record number, and a fingerprint associated with the patient, a fourth validation iteration comprising receiving only the name, the date of birth, the social security number, the medical record number, the fingerprint, and one of facial data or voice data of the patient, wherein a fifth validation iteration comprises receiving only the name, the date of birth, the social security number, the medical record number, the fingerprint, one of the facial data or the voice data, and an iris/retina recognition of the patient, and wherein a sixth validation iteration comprises receiving only the name, the date of birth, the social security number, the medical record number, the fingerprint, one of the facial data or the voice data, an iris/retina recognition of the patient and DNA data associated with the patient.

7. The method of claim 1, wherein validating the patient comprises, when a validation process using the second series of validation iterations comprising the protected health information is not successful, identifying a match by determining whether a cryptographic hash match exists for any of the first biometric data or separately for any of the second biometric data.

8. A system comprising:

a blockchain network comprises a plurality of nodes each running a consensus algorithm to confirm data recorded in a distributed ledger across the plurality of nodes; and one or more hardware processors configured by machine-readable instructions to:

receive, from a patient, first biometric data associated with a first biometric data type and second biometric data associated with a second biometric data type, wherein the first biometric data type differs from the second biometric data type;

generate a cryptographic hash of the first biometric data and the second biometric data to yield a biometric numeric score;

record the biometric numeric score on the blockchain network to yield a recorded biometric numeric score;

receive protected health information for the patient;

generate a protected health information numeric score based on the protected health information for the patient;

record the protected health information numeric score on the blockchain network to yield a recorded protected health information numeric score;

receive and encrypting patient credentials to yield encrypted patient credentials;

record the encrypted patient credentials on the blockchain network to yield recorded encrypted patient credentials;

generate a master cryptographic hash based at least in part on the recorded biometric numeric score, the recorded protected health information and the recorded encrypted patient credentials; and validate, via the blockchain network operating a smart validation contract and upon a request for validation by one of the patient or another person, the patient by using the master cryptographic hash, and based on a series of validation iterations comprising a first series of validation iterations limited to the protected health information, and a second series of validation iterations comprising the protected health information and one or more biometric data types.

9. The system of claim 8, wherein the one or more hardware processors are further configured by machine-readable instructions to generate tokens associated with the master cryptographic hash.

10. The system of claim 9, wherein the tokens can be used to gain access to health information associated with the patient.

11. The system of claim 8, wherein the protected health information comprises one or more of a name of the patient, a date of birth of the patient, a social security number of the patient and a medical record number of the patient.

12. The system of claim 8, wherein validating the patient further comprises applying the first series of validation iterations, wherein the first series of validation iterations comprises a first validation iteration comprising receiving only a name, a date of birth, and a social security number of the patient and wherein a second validation iteration comprises receiving only the name, the date of birth, and a medical record number associated with the patient.

13. The system of claim 12, wherein validating the patient further comprises applying the second series of validation iterations, wherein the second series of validation iterations comprises a third validation iteration comprising receiving only the name, the date of birth, the social security number, the medical record number, and a fingerprint associated with the patient, a fourth validation iteration comprising receiving only the name, the date of birth, the social security number, the medical record number, the fingerprint, and one of facial data or voice data of the patient, wherein a fifth validation iteration comprises receiving only the name, the date of birth, the social security number, the medical record number, the fingerprint, one of the facial data or the voice data, and an iris/retina recognition of the patient, and wherein a sixth validation iteration comprises receiving only the name, the date of birth, the social security number, the medical record number, the fingerprint, one of the facial data or the voice data, an iris/retina recognition of the patient and DNA data associated with the patient.

14. The system of claim 8, wherein validating the patient comprises, when a validation process using the second series of validation iterations comprising the protected health information is not successful, identifying a match by determining whether a cryptographic hash match exists for any of the first biometric data or separately for any of the second biometric data.

15. A method comprising:
receiving personal health information associated with a patient to be validated in a medical record system;
validating, via a blockchain network, the personal health information of the patient by determining whether a match exists with a cryptographic hash of previously entered personal health information of patients, the cryptographic hash being recorded on the blockchain network, wherein the blockchain network comprises a plurality of nodes each running a consensus algorithm to confirm a recorded biometric numeric score being recorded in a distributed ledger across the plurality of nodes; and
when a match exception exists based on the personal health information of the patient, implementing, via the blockchain network operating a smart contract, a process of validation iterations which comprises determining a match of received biometric data from the patient against a cryptographic hash of the recorded biometric numeric score recorded on the blockchain network, wherein the recorded biometric numeric score represents a sub data point representing a type of biometric data used to validate the patient.

16. The method of claim 15, wherein the received biometric data comprises a first type of biometric data, and wherein the biometric numeric score represents a first biometric score recorded on the blockchain network for the first type of biometric data, and wherein the process of validation iterations comprises iteratively matching respective received biometric data from the patient of a respective type of biometric data, wherein each respective type of biometric data is separately cryptographically hashed and recorded on the blockchain network to generate a respective biometric numeric score for the respective type of biometric data and which is recorded on the blockchain network.

17. The method of claim 16, wherein the first type of biometric data comprises a fingerprint, a second type of biometric data comprises one of facial data and/or voice data, a third type of biometric data comprises iris data and/or retina image data, and a fourth type of biometric data comprises DNA data of the patient.

18. The method of claim 17, wherein the process of validation iterations further comprises an ordered series of validation matching operations comprising (1) applying a fingerprint validation, (2) applying the fingerprint validation plus a facial data validation or a voice data validation, (3) applying the fingerprint validation, one of the facial data validation or the voice data validation, and an iris validation or a retina scan validation and (4) applying the fingerprint validation, one of the facial data validation or the voice data validation, an iris validation or a retina scan validation and a DNA validation process for the patient.

19. The method of claim 16, further comprising generating blockchain-based tokens associated with the personal health information.

20. The method of claim 19, further comprising:
receiving a blockchain-based token from an entity; and
providing access to the personal health information of the patient to the entity based on the receiving of the blockchain-based token.

\* \* \* \* \*